United States Patent
Gil et al.

(10) Patent No.: US 8,430,880 B2
(45) Date of Patent: Apr. 30, 2013

(54) DEVICE FOR TRIMMING AN OSTEOCHONDRAL IMPLANT AND A SURGICAL PROCEDURE INVOLVING SAME

(75) Inventors: Carlos E. Gil, Collierville, TN (US); Jeetendra Bharadwaj, Memphis, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 1478 days.

(21) Appl. No.: 11/339,694

(22) Filed: Jan. 25, 2006

(65) Prior Publication Data
US 2007/0173852 A1 Jul. 26, 2007

(51) Int. Cl.
*A61B 17/32* (2006.01)

(52) U.S. Cl.
USPC .................. 606/79; 606/167; 30/289; 30/282

(58) Field of Classification Search ............ 606/79, 606/184, 167; 623/23.63; 30/278, 286, 282, 30/289, 293
See application file for complete search history.

(56) References Cited

U.S. PATENT DOCUMENTS

| 2,737,721 | A | * | 3/1956 | Hart | 83/437.5 |
| 4,513,501 | A | * | 4/1985 | Lee | 30/115 |
| 6,458,144 | B1 | * | 10/2002 | Morris et al. | 606/179 |
| 6,648,894 | B2 | * | 11/2003 | Abdelgany et al. | 606/79 |

OTHER PUBLICATIONS

U.S. Appl. No. 11/340,024, filed Jan. 26, 2006, Nycz, et al.
U.S. Appl. No. 11/339,194, filed Jan. 25, 2006, Nycz, et al.
U.S. Appl. No. 11/338,926, filed Jan. 25, 2006, Bharadwaj, et al.
U.S. Appl. No. 11/317,985, filed Dec. 23, 2005, Lyons.
U.S. Appl. No. 11/340,884, filed Jan. 27, 2006, Shimko, et al.
U.S. Appl. No. 11/343,156, filed Jan. 30, 2006, Bharadwaj, et al.

* cited by examiner

*Primary Examiner* — Eduardo C Robert
*Assistant Examiner* — Julianna N Harvey
(74) *Attorney, Agent, or Firm* — Sorrell, Lenna & Schmidt LLP

(57) ABSTRACT

A device for trimming an osteochondral implant according to which a body member has a bore for receiving the graft and a cutting slot extending transverse to the bore for receiving a cutting blade. A mechanism adjusts the graft in the bore relative to the slot so that the graft can be cut to a predetermined length with the cutting blade in the slot.

21 Claims, 3 Drawing Sheets

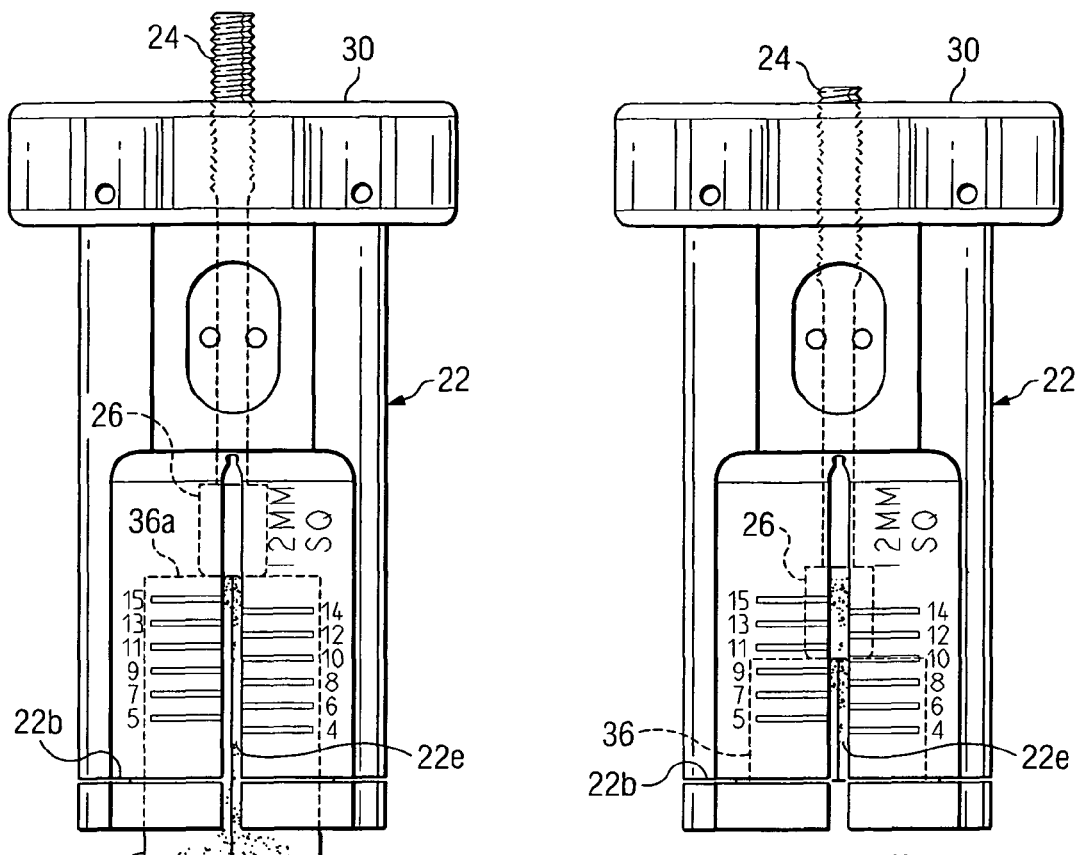
Fig. 5A
Fig. 5B
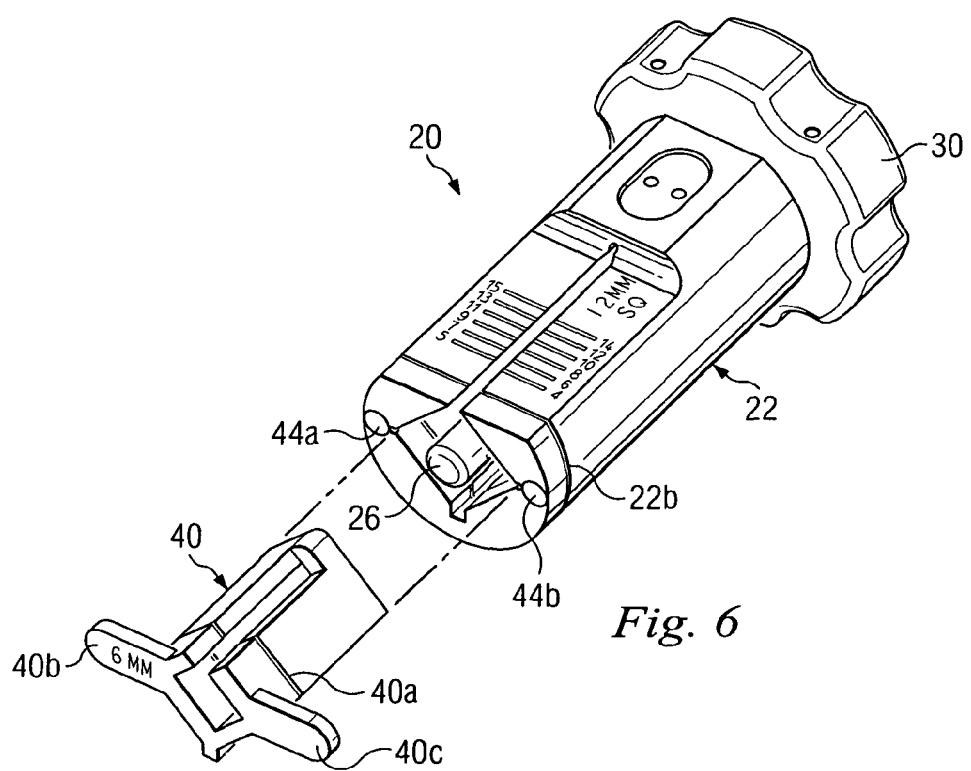
Fig. 6

DEVICE FOR TRIMMING AN OSTEOCHONDRAL IMPLANT AND A SURGICAL PROCEDURE INVOLVING SAME

BACKGROUND

This invention relates to a device for trimming an osteochondral implant and to a surgical procedure involving the trimmed implant.

In the human body, the knee consists of three articulating components—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" and "OATS" has been used to repair articular cartilages. This procedure involves removing injured tissue from the articular defect and drilling cylindrical holes in the base of the defect and underlying bone. Cylindrical plugs, consisting of healthy cartilage overlying bone, are obtained from another area of the patient, typically from a lower-bearing region of the joint under repair, or from a donor patient, and are implanted in the holes.

Often the harvested graft is of a length that is greater than the desired length of the graft to be implanted, and what is needed is a device for trimming a harvested graft to the size desired for the implant.

BRIEF DESCRIPTION OF THE DRAWING

FIGS. 5A and 5B are front elevational views depicting different operational modes of the device of FIGS. 2 and 3.

FIG. 6 is a view similar to that of FIG. 3 but depicting an optional feature for use in the device of FIG. 3.

DETAILED DESCRIPTION

Figure 1:
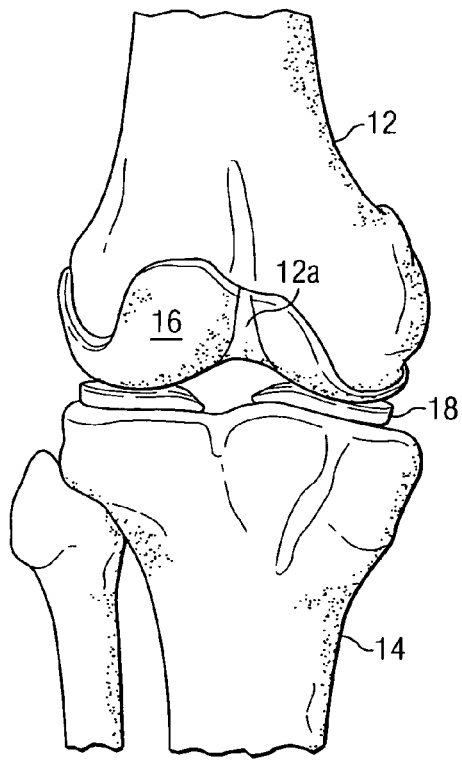
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity to form a joint. A cartilage 16 extends over a portion of the chondral area of the femur 12, and a meniscus 18 overlies a portion of the chondral area of the tibia 14 and extends between the tibia and the cartilage. The patella, as well as the related tendons and quadriceps that also form part of the knee, are not shown in the interest of clarity.

It will be assumed that a portion of the cartilage 16 in the chrondral area of the femur 12 has been damaged and removed by the surgeon, or has worn away, exposing a damaged area, or defect 12a, and that it is desired to implant a graft in the defect. To this end, it is understood that an opening is formed in the defect for receiving the graft.

Figure 2:
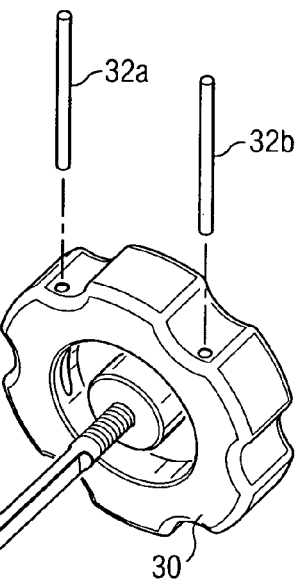
FIG. 2 is an exploded view, illustrating the trimming device according to an embodiment of the invention.
Figure 2:
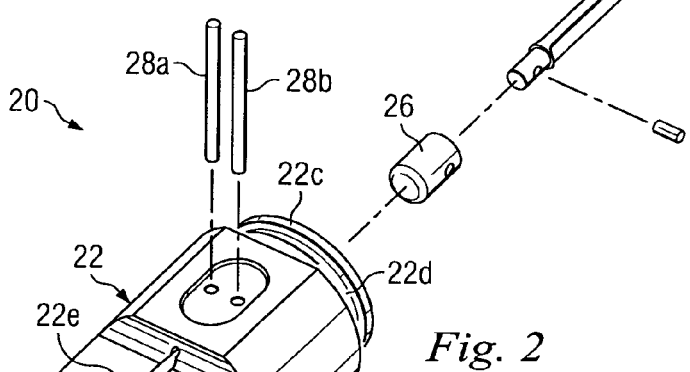
Figure 2:
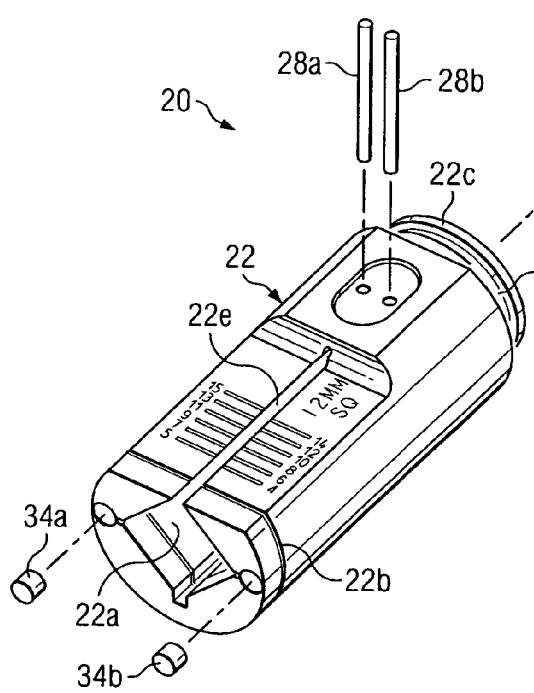

FIG. 2 depicts a device 20 for trimming a graft harvested from an undamaged non-load bearing area of the patient/recipient, or from a donor. The device 20 consists of a cylindrically-shaped body member 22 having a continuous bore 22a formed therein for receiving a harvested graft (not shown). In the example shown, the bore 22a has a rectangular cross-section which corresponds to that of the harvested graft, it being understood that the graft can have a cross-section of a different configuration, such as circular, hexagonal, pentagonal, etc. One end of the bore 22a serves as an inlet for receiving the graft, and a transverse cutting slot 22b extends through the body member 22 in a spaced relation to the inlet for cutting the graft, in a manner to be described.

An annular flange 22c extends from the other end of the body member, and a circumferential groove 22d is formed in the flange. An axially-extending slot 22e is formed through the upper surface of the body member 22, as viewed in the drawing, and indicia is provided on the latter surface of the body member 22 to either side of the slot. In the example shown in the drawings, the indicia indicates the distance, in millimeters, from the slot 22b.

A mechanism is provided for adjusting the position of the graft in the bore 22a and includes a rod 29 adapted to extend in the bore. One end portion of the rod 29 is externally threaded and the other end is adapted to be connected, in any conventional manner, such as by a set screw, to a plunger 26. The outer surfaces of two opposed side portions of the rod 29 are flat, and two dowels 28a and 28b extend through corresponding openings in the body member 22 and engage the flat portions of the rod to prevent rotation of the rod in the body member 22.

A knob 30 has an internally threaded bore in threaded engagement with the threaded end portion of the rod 29. Two dowels 32a and 32b extend through two transverse openings formed in the knob 30 and into the groove 22d. This secures the knob 30 against axial movement relative to the body member 22 while permitting rotational movement.

A pair of magnets 34a and 34b are located in corresponding openings (44and 44b in FIG. 6) formed in the end of the body member 22 adjacent the above inlet of the bore 22a, for reasons to be explained.

Figure 3:
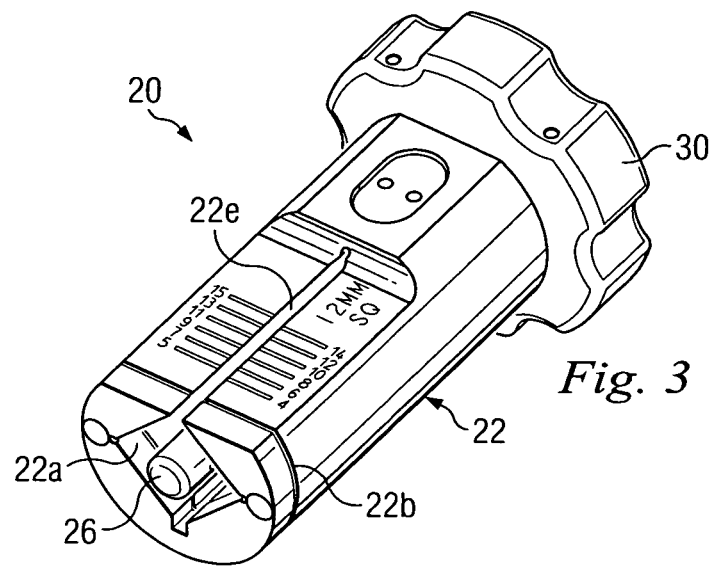
FIG. 3 is a view of the device of FIG. 2 in an assembled condition.

The device 20 is shown in its assembled condition in FIG. 3 with the rod 29 (not shown in FIG. 3, 29 in FIG. 2, 24 in FIG. 5A and 5B)) and therefore the plunger 26, in their fully extended position with the plunger located at the inlet of the bore 22a.

Figure 4:
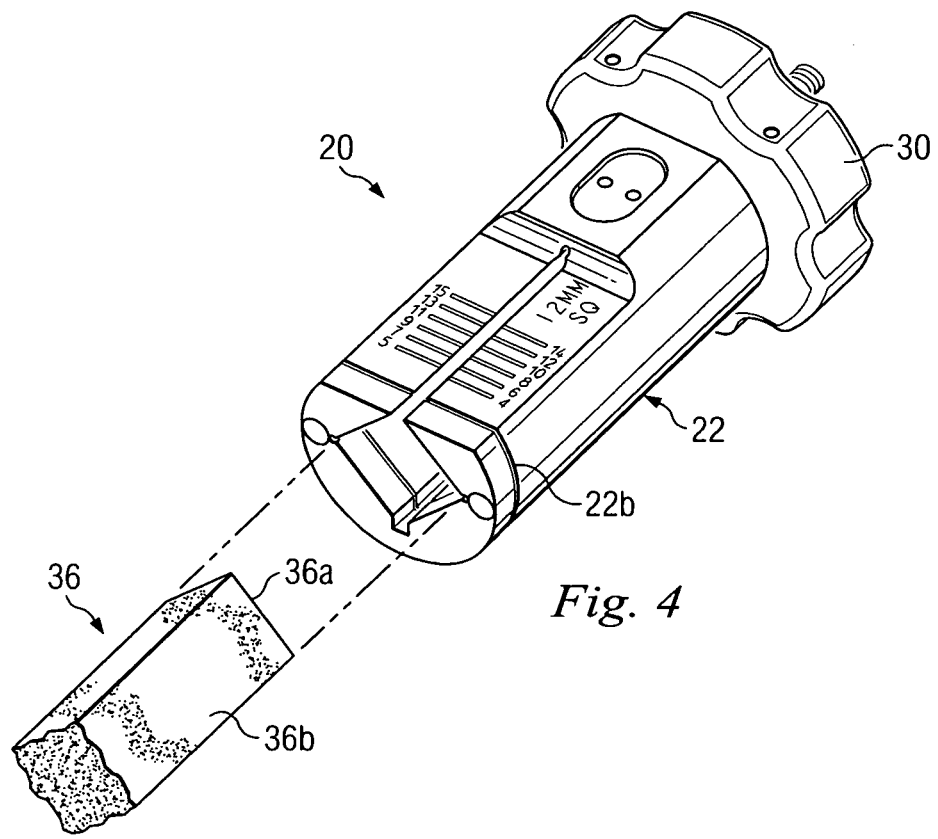
FIG. 4, a view similar to that of FIG. 3, but depicting a different operational mode of the device of FIGS. 2 and 3.

Referring to FIG. 4, it will be assumed that it is desired to trim the length of an osteochondral graft 36, having a cartilage portion 36a overlying an end of a condyle portion 36b. For example, it will be assumed that the graft 36 is approximately 20 millimeters in length and that it is desired to cut it to 10 millimeters in length which corresponds to the depth of the above opening to be formed in the defect 12a (FIG. 1).

Before use, the knob 30 is rotated in a direction to cause axial movement of the rod 29, and therefore the plunger 26, to a fully retracted position, i.e., a position in which the plunger is a maximum distance away from the cutting slot 22b. The graft 36 is then inserted in the bore 22a, with the cartilage portion 36a being inserted first so that it engages the distal end of the retracted plunger 26.

FIG. 5A depicts the plunger 26 in its fully retracted position with its distal end engaging the cartilage portion 36a and with the other end of the graft 36 projecting slightly from the inlet end of the bore 22a. The knob 30 is then rotated to force the rod 24, and therefore the plunger 26 and the graft 36, to move axially in the body member 22 in a direction towards the cutting slots 22b. This movement continues until the interface between the distal end of the plunger 26 and the leading end of the graft 36 align with the 10 millimeter indicia on the body member, as shown in FIG. 5B. A cutting blade (not shown) is then inserted in the slot 22b and forced downwardly into the body member 22 to cut off a portion of the condyle of the graft 36. The remaining portion of the graft 36 in the body member is 10 millimeters in length and is then removed from the body member 22 and implanted in the opening in the defect 12a (FIG. 1).

It is noted that the bore 22a is sized so as to receive a graft of a predetermined cross section, which in the example described above, is a square having a width and height of 12 millimeters. With reference to FIG. 6, if it is desired to cut a graft having a different cross-section, such as a square having a width and height of 6 millimeters, an insert 40 is provided which has external dimensions slightly less than the internal dimensions of the bore 22a so that it can be inserted in the bore with minimum clearance. The insert 40 defines an internal bore having a rectangular cross-section of dimensions corresponding to the dimensions of the graft, which in this example is 6 millimeters square, so as to accommodate the graft with minimum clearance. A transverse cutting slot 40a extends through the insert and is adapted to align with the cutting slot 22b of the body member 22 when the insert is fully inserted in the body member.

A pair of flanges 40b and 40c extend outwardly from the insert and are of a material that is magnetically attracted to the magnets 34a and 34b. Thus, when the insert 40 is inserted in the bore 22a of the body member 22, the flanges 40b and 40c engage the magnets 34a and 34b, respectively, to secure the insert in the bore 22a of the body member 22. The graft 36 is then inserted in the insert 40 and a cutting blade (not shown) is then inserted in the aligned slots 22b and 40a and forced downwardly into the body member 22 to cut off a portion of the condyle of the graft 36.

It can be appreciated that a kit can be provided consisting of the body member 22 and several inserts similar to the insert 40 with each varying with respect to the size and/or shape of the cross-section of its bore, so as to accommodate a plurality of grafts having varying cross-sections.

VARIATIONS

1. The cross-sectional dimensions of the graft to be cut, and therefore the bore 22a and/or the bore in each insert 40, can vary.

2. The cross-section of the graft to be cut, and therefore that of the bore 22a and/or the bore in each insert 40, can vary. For example, the shape can be in the form of a circle, a hexagon, a pentagon, etc.

3. The cross-section of the graft can take any one of the shapes disclosed in co-pending U.S. patent application Ser. No. 11/120,136, filed Apr. 30, 2005, the disclosure of which is incorporated by reference.

4. The spatial references mentioned above, such as "upper", "axial", "transverse", etc., are for the purpose of illustration only and do not limit the specific orientation or location of the components described above.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

The invention claimed is:

1. A device for cutting a graft harvested from a human, the device comprising:
    a body member having a bore configured for receiving a harvested graft, said bore defining a longitudinal axis;
    an elongated rod being disposed in the body member and axially aligned with said bore and configured to move axially in the bore and to engage the graft;
    a cutting slot formed transverse through the body member bore, said cutting slot configured for permitting passage of a cutting blade at least partially through the body and cutting the harvested graft to a predetermined length;
    at least one monolithic insert adapted to be inserted into said body member bore and defining an insert bore to receive said graft of a smaller cross section than the cross-section of said body member bore, said at least one monolithic insert defining a cutting slot formed traverse through said insert that is adapted to align with said cutting slot formed in said body member bore; and
    a mechanism for adjusting the rod with the harvested graft in the body member bore relative to the slot so that the graft can be cut to a predetermined length with the cutting blade in the slot.

2. The device of claim 1 wherein the rod includes a plunger disposed on one end of the rod for engaging the graft.

3. The device of claim 2 wherein the graft is to be implanted in an opening in the human or in another human, and wherein the predetermined length corresponds to the depth of the opening.

4. The device of claim 1 further comprising a slot formed through the body member to enable the position of the rod, and therefore the graft, in the body member to be visually determined.

5. The device of claim 1, comprising a plunger connected to the rod to adapt the rod to engage the graft.

6. The device of claim 1, wherein the body member comprises an axial bore with axial extending slot and inicia, provided on the body member on cooperation with the slot, to indicate location of the graft within the body member for cutting to a selected size.

7. The device of claim 1, comprising a knob threadedly engaging the rod so that rotation of the knob causes corresponding axial movement of the rod in the body member bore to adjust the position of the graft in the bore.

8. A device for cutting a graft harvested from a human, the device comprising:
    a body member having a bore configured for receiving the graft, said bore defining a longitudinal axis;

a cutting slot formed transverse to the bore for receiving a cutting blade, said cutting slot configured for permitting passage of a cutting blade at least partially through the body and cutting the harvested graft to a predetermined length;

at least one monolithic insert to be inserted into said body member bore and defining an insert bore to receive said graft of a smaller cross section than the cross-section of said body member bore, said at least one monolithic insert defining a cutting slot formed traverse through said insert that is adapted to align with said cutting slot formed in said body member bore; and means for adjusting the graft in the body member bore or said insert bore relative to the cutting slot, the means configured to move axially in the body member bore or said insert bore and to engage the graft and to position the graft so that the graft can be cut to a predetermined length with the cutting blade in the cutting slot.

9. The device of claim 8 wherein the means comprises a rod disposed in the bore and adapted to be engaged by the graft, a knob threadedly engaging the rod so that rotation of the knob causes corresponding axial movement of the rod in the bore to adjust the position of the graft in the bore.

10. The device of claim 9 wherein the rod includes a plunger disposed on one end of the rod for engaging the graft.

11. The device of claim 9 further comprising a slot formed through the body member to enable the position of the rod, and therefore the graft, in the body member to be visually determined.

12. The device of claim 8 wherein the graft is to be implanted in an opening in the human or in another human, and wherein the predetermined length corresponds to the depth of the opening.

13. The device of claim 8 wherein the cross-section of the bore is sized to accommodate the graft with minimal clearance, and the device further comprises an insert adapted to be inserted into the bore and defining another bore to receive a graft of a smaller cross-section.

14. A kit for use in a surgical procedure, the kit comprising:
a body member having a bore configured for receiving a graft to be implanted in a human;
an elongated rod being disposed in the body member bore and axially aligned with said bore configured to move axially in the bore and to engage the graft a cutting slot formed transverse to the body member bore for receiving a cutting blade, said cutting slot configured for permitting passage of said cutting blade at least partially through the body member bore so as to permit cutting of said harvested graft to a predetermined length;

a plurality of varying cross-sectioned monolithic inserts each monolithic insert adapted to fit in the body member bore and defines another bore configured to receive a graft of a smaller cross section than the cross-section of said body member bore, said monolithic inserts further comprising a cutting slot formed traverse through said inserts that is adapted to align with said cutting slot formed in said body member bore; and a mechanism for adjusting the graft in the bore of the insert relative to the cutting slot so that the graft can be cut to a predetermined length with the cutting blade in the slot.

15. The kit of claim 14 wherein the cross-sectional dimensions of the bore of each insert are different from those of the bores of the other inserts so that grafts having varying cross-sectional dimensions can be accommodated.

16. The kit of claim 14 wherein the rod includes a plunger disposed on one end of the rod for engaging the graft.

17. The kit of claim 14, further comprising a slot formed through the body member to enable the position of the rod, and therefore the graft, in the body member to be visually determined.

18. The kit of claim 14 wherein the graft is to be implanted in an opening in the human or in another human, and wherein the predetermined length corresponds to the depth of the opening.

19. The kit of claim 18, wherein the body member comprises a plunger connected to the rod to adapt the rod to engage the graft.

20. The kit of claim 14, wherein the body member comprises an axial bore with axial extending slot and indicia provided on the body member in cooperation with the slot, to indicate location of the graft within the body member for cutting to a selected size.

21. the kit of claim 14, comprising a knob threadedly engaging the rod so that rotation of the knob causes corresponding axial movement of the rod in the body member bore to adjust the position of the graft in the bore.

* * * * *